United States Patent [19]
Alexander

[11] 3,966,762
[45] June 29, 1976

[54] N-[6,7]-DIHYDROINDOLO[1,7-ab][1]BENZAZEPIN-2-YL[METHYL]PHTHALIMIDE

[75] Inventor: John Ernest Alexander, East Greenbush, N.Y.

[73] Assignee: Sterling Drug Inc., New York, N.Y.

[22] Filed: June 3, 1974

[21] Appl. No.: 475,445

[52] U.S. Cl. .................. 260/326.D; 260/268 PC; 260/293.61; 260/326.9; 424/250; 424/267; 424/274
[51] Int. Cl.² ........................................ C07D 403/00
[58] Field of Search .............. 260/268 PC, 326.15, 260/293.61, 326 D

[56] References Cited
UNITED STATES PATENTS 3,642,779  2/1972  Duncan et al. ................ 260/326.15
3,784,548  1/1974  Yale et al. ..................... 260/268 PC
3,813,396  5/1974  Yale et al. ..................... 260/268 PC

OTHER PUBLICATIONS

Cattanach et al., J. Chem. Soc. Perkin I, 1041–1047, (1973).

Chem. Abstracts, 60:2916, (1963).

Primary Examiner—R. Gallagher
Attorney, Agent, or Firm—Frederik W. Stonner; B. Woodrow Wyatt

[57]  ABSTRACT

Novel 2-(aminoalkyl)-6,7-dihydroindolo[1,7-ab][1]benzazepines and acid-addition salts thereof having antibacterial activity, and intermediate and process for the preparation thereof are disclosed.

1 Claim, No Drawings

N-[6,7]-DIHYDROINDOLO[1,7-AB][1]BENZAZE-PIN-2-YL)METHYL]PHTHALIMIDE

The invention sought to be patented resides in one aspect in the chemical compounds designated 2-[(CH$_2$)$_n$N=B] 1-R-6,7-dihydroindolo[1,7-ab][1]benzazepines having the formula:

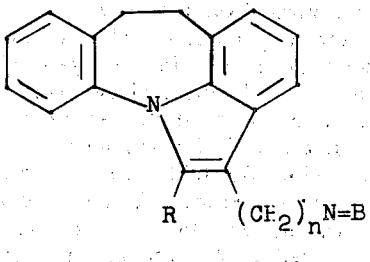

where R is hydrogen, N=B is amino and n is the integer 1; or R is methyl,
N=B is selected from 4-phenyl-1-piperazinyl and piperidino, and n is the integer 2; and acid-addition salts thereof.

The compounds of the invention having formula I and acid-addition salts thereof exhibit antibacterial activity as more fully described hereinbelow.

The invention sought to be patented resides in another aspect in the chemical compound designated N-[(6,7-dihydroindolo[1,7-ab][1]benzazepin-2-yl)methyl]phthalimide having the formula:

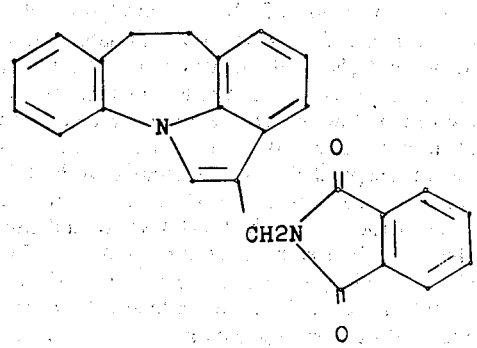

The compound of formula II is useful as an intermediate for the preparation of the compound of formula I where N=B is amino.

The compounds of formula I, where N=B is 4-phenyl-1-piperazinyl and piperidino, and the compound of formula II are prepared by the Fischer indole synthesis. Thus they are prepared by condensing 5-amino-10,11-dihydro-5H-dibenz[b,f] azepine with the appropriate known aldehyde or ketone having the formula R-CO-(CH$_2$)$_m$A, where R is H, m is the integer 2 and A is phthalimido; or R is methyl, m is the integer 3, and A is 4-phenyl-1-piperazinyl or piperidino.

The compound of formula I where N=B is amino is prepared from the phthalimido compound II by treatment with a suitable basic agent, e.g., hydrazine or aqueous alkali such as potassium hydroxide at elevated temperatures, in a suitable solvent.

The compounds of the invention having formula I are useful both in the free base form and in the form of acid-addition salts, and both forms are within the pur-view of the invention. The acid-addition salts are simply a more convenient form for use, and in practice, use of the salt form inherently amounts to use of the base form. When the compounds of the invention having formula I are to be utilized for pharmaceutical purposes, the acids which can be used to prepare the acid-addition salts include preferably those which produce, when combined with the free base, medicinally acceptable salts, that is, salts whose anions are relatively innocuous to the animal organism in medicinal doses of the salts, so that the beneficial properties inherent in the free base are not vitiated by side effects ascribable to the anions. Appropriate medicinally acceptable salts within the scope of the invention are those derived from mineral acids such as hydrochloric acid, hydrobromic acid, hydriodic acid, nitric acid, phosphoric acid, sulfamic acid, and sulfuric acid; and organic acids such as acetic acid, citric acid, tartaric acid, lactic acid, cyclohexanesulfamic acid, methanesulfonic acid, ethanesulfonic acid, benzenesulfonic acid, p-toluenesulfonic acid, quinic acid, and the like, giving the hydrochloride, hydrobromide, hydriodide, nitrate, phosphate, sulfamate, acetate, citrate, tartrate, lactate, cyclohexanesulfamate, methanesulfonate, ethanesulfonate, benzenesulfonate, p-toluenesulfonate and quinate respectively.

The acid-addition salts of said basic compounds are prepared either by dissolving the free base in aqueous or aqueous-alcohol solution containing the appropriate acid and isolating the salt by evaporating the solution, or by reacting the free base and acid in an organic solvent, in which case the salt separates directly or can be obtained by concentration of the solution or dilution of the solution with a solvent in which the salt is insoluble or only slightly soluble.

Although medicinally acceptable salts of said basic compounds are preferred for pharmaceutical purposes, all acid-addition salts are within the scope of the invention. All acid-addition salts are useful as sources of the free base form even if the particular salt per se is desired only as an intermediate product as for example when the salt is formed only for purposes of purification or identification, or when it is used as an intermediate in preparing a medicinally acceptable salt by ion exchange procedures.

The compounds of formula I and acid-addition salts thereof possess useful antibacterial activity, thus indicating the utility of the compounds of formula I and acid-addition salts thereof as antibacterial agents.

The antibacterial activities were determined using a modification of the Autotiter method described by Goss et al., Applied Microbiology 16 (No. 9), 1414–1416 (1968) in which a 1000 mcg./ml. solution of the test compound is prepared. To the first cup of the Autotray is added 0.1 ml. of the test solution. Activation of the Autotiter initiates a sequence of operations by which 0.05 ml. of the test compound solution is withdrawn from this cup by a Microtiter transfer loop and diluted in 0.05 ml. of sterile semi-synthetic medium (glucose). After this operation, 0.05 ml. of inoculated semisynthetic medium is added automatically to each cup. The overall operation results in final drug concentrations ranging from 500 to 0.06 mcg./ml. in twofold decrements. The Autotray is incubated for 18–20 hours at 37°C., at which time the trays are examined visually for growth as evidenced by turbidity, and the concentration of the last sample in the series showing no growth (or no turbidity) is recorded as the minimal inhibitory concentration (MIC).

The compound of Example 1 was found to be antibacterially effective against *Pseudomonas aeruginosa* at a concentration of 125 mcg./ml. The compound of Example 2 was found to be antibacterially effective against *Staphylococcus aureus*, *Pseudomonas aeruginosa* and *Escherichia coli* at concentrations of 31.3 mcg./ml., 125 mcg./ml., and 125 mcg./ml. respectively. The compound of Example 3B was found to be antibacterially effective against *Staphylococcus aureus*, *Pseudomonas aeruginosa*, *Escherichia coli*, and *Proteus vulgaris* at concentrations of 62.5 mcg./ml., 125 mcg./ml., 62.5 mcg./ml. and 125 mcg./ml. respectively.

The actual determination of the numerical biological data definitive for a particular compound is readily determined by standard test procedures by technicians having ordinary skill in pharmacological test procedures, without the need for any extensive experimentation.

The compounds of the invention having formula I can be formulated for use by preparing a dilute solution in an aqueous medium or in a solution containing a surfactant, or alternatively in an organic medium in which the compounds are soluble, for example ethyl alcohol, and are applied to a surface to be disinfected by conventional means such as spraying, swabbing, immersion, and the like. Alternatively, the compounds can be formulated as ointments or creams by incorporating them in conventional ointment or cream bases, for example alkylpolyether alcohols, cetyl alcohol, stearyl alcohol, and the like, or as jellies by incorporating them in conventional jelly bases as glycerol and tragacanth. They can also be formulated for use as aerosol sprays or foams.

The molecular structures of the compounds of the invention were assigned on the basis of the method of their synthesis and study of their infrared spectra, and confirmed by the correspondence between calculated and found values for the elementary analysis.

The invention is illustrated by the following examples without, however, being limited thereto.

EXAMPLE 1

A suspension of 5-amino-10,11-dihydro-5H-dibenz[b,f]azepine hydrochloride (5.0g.) and 5-(4-phenyl-1-piperazinyl)-2-pentanone monohydrate monohydrochloride (6.2g.) in absolute alcohol (100 ml.) was heated on a water bath at 50° to 60°C. in a nitrogen atmosphere for one hour. The mixture was cooled and the solids were collected by filtration, washed with ethyl alcohol, suspended in aqueous methyl alcohol, collected by filtration, washed with water, ethyl alcohol and ether to give 2-[(4-phenyl-1-piperazinyl)-ethyl]-1-methyl-6,7-dihydroindolo-[1,7-ab][1]benzazepine hydrochloride (4.4g.), m.p. 280°–288°C.(dec.). By treatment of this hydrochloride salt in water with an equivalent of ammonium hydroxide and isolation using standard procedures there is obtained the free base 2-[(4-phenyl-1-piperazinyl)-ethyl]-1-methyl-6,7-dihydroindolo[1,7-ab][1]benzazepine.

EXAMPLE 2

A solution of 5-piperidino-2-pentanone hydrochloride (3.4g.) and 5-amino-10,11-dihydro-5H-dibenz[b,f]azepine hydrochloride (4.2g.) in isopropyl alcohol (50 ml.) was warmed on a steam bath in a nitrogen atmosphere for thirty minutes, cooled and treated with concentrated ammonium hydroxide. The resulting mixture was extracted with ether and the ether extract was washed with water and dried. The resulting solution in ether of the free base 2-(2-piperidinoethyl)-1-methyl-6,7-dihydroindolo[1,7-ab][1]benzazepine was treated with ethanolic hydrogen chloride. The precipitate was collected and a suspension thereof in acetone-isopropyl alcohol was heated, cooled, filtered and recrystallized from methyl alcohol to give 2-(2-piperidinoethyl)-1-methyl-6,7-dihydroindolo[1,7-ab][1]benzazepine hydrochloride (2.5g.), m.p. 291°–293°C.

EXAMPLE 3

A. Following a procedure similar to that described in Example 1 and using 5-amino-10,11-dihydro-5H-dibenz[b,f]-azepine hydrochloride (5g.) and B-phthalimidopropaldehyde (4.1g.) in glacial acetic acid (75 ml.) there was obtained N-[(6,7-dihydroindolo[1,7-ab][1]benzazepine-2-yl)methyl]phthalimide (5.0g.), m.p. 190°–191°C. (dimethylformamide-ethyl alcohol-water/7.5:1:3).

B. A suspension of N-[(6,7-dihydroindolo[1,7-ab][1]benzazepin-2-yl)methyl]phthalimide(5.0g.) in methyl alcohol (500 ml.) containing 100% hydrazine hydrate (5 ml.) was heated at reflux on a steam bath for five and one-half hours. The solution was evaporated to dryness under reduced pressure and the resulting solid residue was suspended in water, treated with 10% potassium hydroxide solution, and extracted with ether. The ether extract was washed with water and the resulting solution of the free base 2-(aminomethyl)-6,7-dihydroindolo[1,7-ab][1]benzazepine was treated with the minimum required 10% hydrogen chloride to precipitate the hydrochloride salt. This was collected and recrystallized from ethyl alcohol-ether to give 2-(aminomethyl)-6,7-dihydroindolo[1,7-ab][1]benzazepine hydrochloride (6.3g.), m.p. 239°–244°C.

The free base forms of the compounds of the invention obtained as described above can be converted to any desired acid-addition salt, for example, hydrobromide, sulfamate, tartrate, lactate and the like in the manner hereinabove described.

I claim:

1. N-[(6,7-Dihydroindolo[1,7-ab][1]benzazepin-2-yl)methyl]phthalimide.

* * * * *

UNITED STATES PATENT AND TRADEMARK OFFICE
CERTIFICATE OF CORRECTION

PATENT NO. : 3,966,762
DATED : June 29, 1976
INVENTOR(S) : Ernest John Alexander It is certified that error appears in the above—identified patent and that said Letters Patent are hereby corrected as shown below:

The inventor's name should read -- Ernest John Alexander -- and not "John Ernest Alexander".

Signed and Sealed this

Twenty-third Day of November 1976

[SEAL]

Attest:

RUTH C. MASON
*Attesting Officer*

C. MARSHALL DANN
*Commissioner of Patents and Trademarks*